United States Patent
Hara et al.

(10) Patent No.: US 7,393,104 B2
(45) Date of Patent: Jul. 1, 2008

(54) OPHTHALMIC TESTING UNIT AND OPHTHALMIC TESTING EQUIPMENT

(75) Inventors: Takuya Hara, Hamamatsu (JP);
Yoshikatsu Suzumura, Hamamatsu (JP)

(73) Assignee: Kowa Company, Ltd. (JP)

( * ) Notice: Subject to any disclaimer, the term of this patent is extended or adjusted under 35 U.S.C. 154(b) by 184 days.

(21) Appl. No.: 11/238,367

(22) Filed: Sep. 29, 2005

(65) Prior Publication Data
US 2007/0013870 A1 Jan. 18, 2007

(30) Foreign Application Priority Data
Jul. 14, 2005 (JP) ............... 2005-205535

(51) Int. Cl.
*A61B 3/02* (2006.01)
(52) U.S. Cl. .................. 351/239; 351/222
(58) Field of Classification Search ......... 351/222–223, 351/226, 237–239
See application file for complete search history.

(56) References Cited

U.S. PATENT DOCUMENTS

| | | | | |
|---|---|---|---|---|
| 5,519,461 A | * | 5/1996 | Kawamoto et al. | 351/244 |
| 5,694,199 A | * | 12/1997 | Rodriguez | 351/223 |
| 5,956,121 A | * | 9/1999 | Hosoi et al. | 351/205 |
| 5,993,001 A | * | 11/1999 | Bursell et al. | 351/212 |
| 6,406,147 B1 | * | 6/2002 | Hayashi et al. | 351/239 |
| 2001/0043309 A1 | * | 11/2001 | Hayashi et al. | 351/243 |
| 2004/0141152 A1 | * | 7/2004 | Marino et al. | 351/222 |
| 2004/0239878 A1 | * | 12/2004 | Bradley | 351/237 |

* cited by examiner

*Primary Examiner*—Scott J. Sugarman
*Assistant Examiner*—Dawayne A Pinkney
(74) *Attorney, Agent, or Firm*—Fish & Richardson P.C.; Michael W. Tieff

(57) ABSTRACT

When a Landolt ring optotype is presented in a visual acuity testing unit, an examinee answers a position of a slit of the optotype through an operation of a joystick lever or the like. If an examinee gives a right answer within a standard time at a first presentation of optotype, examination at a higher visual acuity grade is executed by presenting a smaller Landolt ring optotype. In case of a right answer over the standard time, reexamination at the same visual acuity grade is executed twice at the most. If a right answer is given at least once, examination at a higher visual acuity grade is executed. In case of a wrong answer within the standard time at a first presentation of optotype, reexamination at the same visual acuity is executed only once. If the right answer is given at this reexamination, examination at a higher visual acuity grade is executed. Reexamination is thus executed, so that the result of the examination is correct. In addition, the examination time can be shortened since necessary number of times of reexaminations is minimum.

5 Claims, 14 Drawing Sheets

FIG. 2

| | FIRST PRESENTATION OF OPTOTYPE | | SECOND PRESENTATION OF OPTOTYPE | THIRD PRESENTATION OF OPTOTYPE | |
|---|---|---|---|---|---|
| | RIGHT ANSWER? | WITHIN TIME? | RIGHT ANSWER? | RIGHT ANSWER? | |
| A | ○ | ○ | — | — | EXAMINATION OF HIGHER VISUAL ACUITY VALUE |
| | ○ | × | ○ | — | EXAMINATION OF HIGHER VISUAL ACUITY VALUE |
| B | ○ | × | × | ○ | EXAMINATION OF HIGHER VISUAL ACUITY VALUE |
| | ○ | × | × | × | END |
| | × | ○ | ○ | — | EXAMINATION OF HIGHER VISUAL ACUITY VALUE |
| C | × | ○ | × | — | END |
| | × | × | ○ | — | END |
| D | × | × | ○ | × | END |
| | × | × | ○ | ○ | EXAMINATION OF HIGHER VISUAL ACUITY VALUE |

FIG. 12
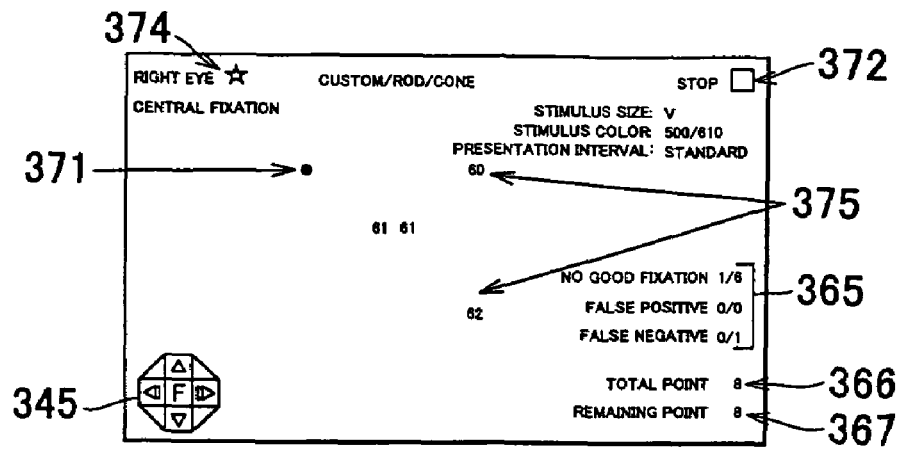
(a) SCREEN DURING MEASUREMENT FOR 500nm
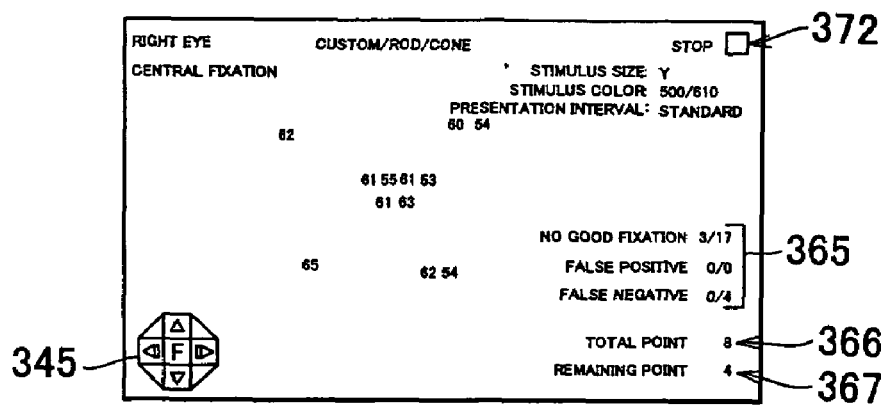
(b) SCREEN DURING MEASUREMENT FOR 610nm
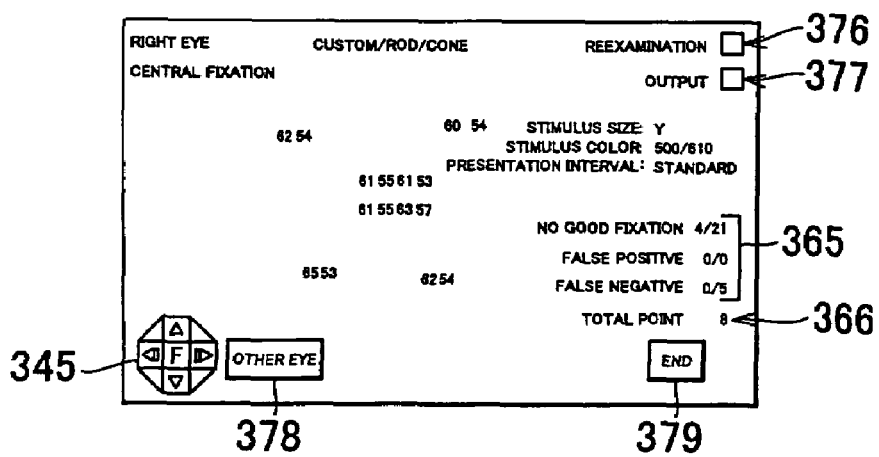
(c) SCREEN AT END OF MEASUREMENT

OPHTHALMIC TESTING UNIT AND OPHTHALMIC TESTING EQUIPMENT

TECHNICAL FIELD

This invention relates to an ophthalmic testing unit for measuring a visual acuity and a visual field of an examinee. And, the invention relates to a visual acuity testing device for testing a visual acuity and a visual acuity testing equipment with the visual acuity testing devices. Besides, the invention relates to a visual field device for measuring a visual field of an examinee.

BACKGROUND ART

A conventional automatic visual acuity testing device which has been proposed shows optotypes to an examinee and automatically tests a visual acuity of the examinee (see Japanese patent application (publication No. H09-1187423, for instance).

FIG. 5 is a perspective view showing appearances of a conventional structure of such an automatic visual acuity testing device. A reference numeral 200 is an optotype portion for showing an optotype, such as a Landolt ring, which is inside a housing 201, and a reference numeral 202 is a test window through which an examinee looks into the optotype portion 200, and a reference numeral 203 is a joystick lever to be operated by an examinee for inputting results of recognition of the optotypes. This kind of the automatic visual acuity testing device has such a structure that input of judgment results of optotypes by an examinee through an operation of the joystick lever 203 in a state that the examinees looks into the optotype portion 200 through the test window 202 causes output of tested results through a printer When suffering from an ophthalmic disease, such as glaucoma and diabetic retinopathy, it is known that a person has a narrow visual field or a lacked visual field. For these reasons, visual field devices having various structures have been proposed as devices for finding such diseases (see Japanese patent application the publication number of which is 2002-272685).

FIG. 14 is a typical view showing a structure of a conventional visual field device. In FIG. 14, a reference numeral 400 denotes a projection optical system for projecting stimuli A, and a reference numeral 401 denotes a visual field dome in the shape of a semi-sphere for projecting stimuli. And, a reference numeral 403 is a response switch to be operated by an examinee.

When starting the visual field device in such a state that an examinee fixates a fixation point inside the visual field dome 401, the projection optical system 400 successively displays stimuli A at various positions of the visual field dome 401. An examinee operates the response switch 403 when perceiving the stimulus A, but does not operate when not perceiving. The visual field of an examinee can be measured from displayed positions of the stimuli A.

When an examinee can not immediately perceive too small optotype in the above-mentioned automatic visual acuity testing device, the examinee may operate the joystick lever 203 after taking a longer time, hesitating to respond. In addition, an examinee may give a wrong answer due to error operation of the joystick lever 203 even if the examinee fully recognizes the optotype. Problems remain if the visual acuity is determined only by right or wrong answer of the result of perception of optotype in such cases.

Generally, an examinee immediately operates the response switch 403 when clearly perceiving the stimulus A and slowly operates the response switch 403, hesitating to answer when faintly perceiving the stimulus in the above-mentioned visual field device. A conventional device measures a visual field without considering a time till the operation of the response switch 403, so that proceeding of the examination is not effective.

The object of the invention is to provide a visual acuity testing device for accurately testing a visual acuity, and a visual acuity testing equipment with the visual acuity testing devices.

Besides, the object of the invention is to provide a visual field device for effectively testing a visual field.

DISCLOSURE OF INVENTION

One aspect of the invention is ophthalmic testing unit, comprising:

optotype presentation means for presenting optotypes to an examinee;

operation means to be operated by said examinee, for outputting a result of perception of said optotype by said examinee as a signal;

response time measuring means for measuring a response time from presentation of said optotype by said optotype presentation means till output of a signal by said operation means;

standard time output means for outputting a standard time with respect to said response time;

time comparison means for comparing a result of measurement by said response time measuring means and said standard time which is outputted from said standard time output means with each other; and optotype change means for changing said optotype which is presented by said optotype presentation means into one which is harder to be perceived for said examinee if said time comparison means judges said response time to be shorter than said standard time.

According to this aspect of the invention, a visual acuity can be accurately examined, taking length of a response time into consideration.

Another aspect of the invention is ophthalmic testing unit having optotype presentation means for presenting optotypes to an examinee, operation means to be operated by said examinee, for outputting a result of perception of said optotype by said examinee as a signal, and optotype perception judging means for judging perception of said optotype by said examinee by comparing signals from said optotype presentation means and said operation means with each other, comprising:

response time measuring means for measuring a response time from a first presentation of said optotype by said optotype presentation means till output of a signal by said operation means;

standard time output means for outputting a standard time with respect to said response time;

time comparison means for comparing a result of measurement by said response time measuring means and said standard time which is outputted from said standard time output means with each other;

first optotype change means for changing said optotype which is presented by said optotype presentation means into a smaller one;

second optotype change means for changing said optotype which is presented by said optotype presentation means into one having the same size and a different shape;

first test control means for driving said first optotype change means so as to examine a higher visual acuity grade when obtaining both judgments, a judgment of a result of said first perception of said optotype to be right by said optotype perception judging means and a judgment of said response time to be shorter than said standard time by said time comparison means; and second test control means for driving said second optotype change means so as to execute reexamination at the same visual acuity grade when not obtaining either of said both judgments, said judgment of said result of said first perception of said optotype to be right and said judgment of said response time to be shorter than said standard time.

According to this aspect of the invention, the same visual acuity grade is tested again if the response time is too long or the result of the perception of the optotype is wrong, so that the accuracy of visual acuity test can be improved in comparison with the test having no such reinspection. If an examinee can not immediately perceive too small optotype and responds after taking a longer time, hesitating to respond, for instance, the test is executed again even if the result of the perception of the optotype is right, so that the accuracy of the visual acuity test can be improved. And, the test is executed again if an examinee makes a wrong answer due to an operation error of the operation means although the examinee completely perceives the optotype, so that the accuracy of the visual acuity test can be improved. On the contrary, time for examination can be shortened by the time for reexamination if the response time is shorter and the result of the perception of the optotype is right since no reexamination does not almost lead to deterioration of testing accuracy.

Another aspect of the invention is the ophthalmic testing unit, further comprising reexamination frequency determining means for determining maximum number of times of reexamination at the same visual acuity grade, memory means for storing a standard right answer percentage on a right answer percentage at a time of said reexamination, and right answer percentage computing means for computing an actual right answer percentage at a time of said reexamination, wherein said first test control means drives said first optotype change means so as to examine a higher visual acuity grade if said right answer percentage computed by said right answer percentage computing means is higher than said standard right answer percentage which is stored in said memory means.

According to this aspect of the invention, an examinee can gradually receive examination at the higher visual acuity grade if the examinee can perceive the optotype either at the time of first presentation of the optotype or at the time of reexamination. Then, the highest visual acuity grade of an examinee can be obtained by repeating such examinations.

Another aspect of the invention is the ophthalmic testing unit, said memory means stores a) a first standard right answer percentage, b) a second standard right answer percentage and c) a third standard right answer percentage, said first standard right answer percentage being applied when obtaining said both judgments, said judgment of said result of said first perception of said optotype to be right and said judgment of said response time to be longer than said standard time, said second standard right answer percentage being applied when obtaining said both judgments, said judgment of said result of said first perception of said optotype to be wrong and said judgment of said response time to be shorter than said standard time, said third standard right answer percentage being applied when obtaining said both judgments, said judgment of said result of said first perception of said optotype to be wrong and said judgment of said response time to be longer than said standard time, said ophthalmic testing unit further comprising judged contents confirming means for confirming contents judged by said optotype perception judging means and contents judged by said time comparison means, and right answer percentage selection instructing means for selectively reading said first through third standard right answer percentages out of said memory means according to a result confirmed by said judged contents confirming means, wherein said first test control means drives said first optotype change means so as to examine a higher visual acuity grade if said right answer percentage computed by said right answer computing means is higher than said standard right answer percentage read out of said right answer percentage selection instructing means.

According to this aspect of the invention, in case of right answer and longer time for response, "examination at a higher visual acuity grade" can be received even if the right answer percentage is lower at the time of reexamination in comparison with a case of wrong answer and longer time for response. In a case where the result of the perception of the optotype is right, an examinee is considered to have a visual acuity higher than one of an examinee who gives a wrong answer. Therefore, lower standard right answer percentage at the time of reexamination does not lead to deterioration of the examination accuracy.

Another aspect of the invention is the ophthalmic testing unit, wherein said reexamination frequency determining means executes a reexamination at the same visual acuity grade only once if said judged contents confirming means judges said result of said first perception of said optotype to be wrong and said response time to be shorter than said standard time, and said memory means outputs 100 percent as said second standard right answer percentage, and said first test control means drives said first optotype change means so as to examine a higher visual acuity grade if a right answer is given at said reexamination executed once.

According to this aspect of the invention, the standard right answer percentage is switched according to the result of the first perception of the optotype, so that proper visual acuity examination is possible.

Another aspect of the invention is the ophthalmic testing unit, wherein said optotype presentation means is means for presenting Landolt ring optotype to said examinee, and said first optotype change means changes said presented Landolt ring optotype into a smaller one, and said second optotype change means changes said presented Landolt ring optotype into one having the same size and a different direction.

According to this aspect of the invention, the same visual acuity grade is tested again if the response time is too long or the result of the perception of the optotype is wrong, so that the accuracy of visual acuity test can be improved in comparison with the test having no such reinspection. If an examinee can not immediately perceive too small optotype and responds after taking a longer time, hesitating to respond, for instance, the test is executed again even if the result of the perception of the optotype is right, so that the accuracy of the visual acuity test can be improved. And, the test is executed again if an examinee makes a wrong answer due to an operation error of the operation means although the examinee completely perceives the optotype, so that the accuracy of the visual acuity test can be improved. On the contrary, time for examination can be shortened by the time for reexamination if the response time is shorter and the result of the perception of the optotype is right since no reexamination does not almost lead to deterioration of testing accuracy.

Another aspect of the invention is ophthalmic testing equipment, comprising:

two or more ophthalmic testing units each having optotype presentation means for presenting an optotype to an examinee and operation means to be operated by said examinee for outputting a result of perception of said optotype by said examinee as a signal;

a central control unit being connected with said two or more ophthalmic testing units;

optotype perception judging means for judging said perception of said optotype by said examinee by comparing signals from said optotype presentation means and said operation means with each other;

response time measuring means for measuring a response time from first presentation of said optotype by said optotype presentation means till output of a signal from said operation means;

standard time output means for outputting a standard time with respect to said response time;

time comparison means for comparing a measured result by said response time measuring means and said standard time outputted by said standard time output means with each other;

first optotype change means for changing said optotype presented by said optotype presentation means into a smaller one;

second otpotype change means for changing said optotype presented by said optotype presentation means into one having the same size and a different shape;

first test control means for driving said first optotype change means so as to examine a higher visual acuity grade when obtaining both judgments, a judgment of a result of said first perception of said optotype to be right by said optotype perception judging means and a judgment of said response time to be shorter than said standard time by said time comparison means; and second test control means for driving said second optotype change means so as to execute reexamination at the same visual acuity grade when not obtaining at least one of said both judgments, said judgment of said result of said first perception of said optotype to be right by said optotype perception judging means and said judgment of said response time to be shorter than said standard time by said time comparison means;

wherein said optotype perception judging means, said response time measuring means, said standard time output means, said time comparison means, said first optotype change means, said second optotype change means, said first test control means and said second test control means are respectively arranged at either said ophthalmic testing unit or said central control unit.

According to this aspect of the invention, visual acuity tests by two or more visual acuity testing devices can be unitarily controlled with the central control unit, so that works or time for the visual acuity test can be decreased.

Another aspect of the invention is ophthalmic testing unit for measuring a visual field of an examinee by successively displaying stimuli having predetermined luminances at various positions in said visual field of said examinee, comprising:

stimulus display means being comprised of a stimulus presentation portion for presenting said stimulus in said visual field of said examinee, a displayed position change portion for changing a displayed position of said stimulus, and a luminance setting portion for setting said luminance of said stimulus;

operation means to be operated by said examinee who have perceived said stimulus displayed;

a signal output portion for outputting a signal when said operation means being operated;

a visual field judging portion for judging said visual field of said examinee when said signal being outputted from said signal output portion;

a response time measuring portion for measuring a response time from presentation of said stimulus by said stimulus display means till output of said signal from said signal output portion;

a standard time output portion for outputting a standard time which is a basis for judging whether or not said luminance setting portion should change said luminance of said stimulus; and a time comparison portion for comparing said response time and said standard time with each other;

wherein said luminance setting portion darkens said luminance of said stimulus by a first predetermined volume if said time comparison portion judges said response time to be shorter than said standard time, and darkens said luminance of said stimulus by a second predetermined volume if said time comparison portion judges said response time to be longer than said standard time.

According to this aspect of the invention, a visual field of an examinee is judged by not only simple judgment of the result of an examinee's perception of stimulus, but also by a time for perceiving stimuli (that is, the response time), so that the measurement accuracy can be improved.

Another aspect of the invention is the ophthalmic testing unit, wherein said first predetermined volume is more than said second predetermined volume.

According to this aspect of the invention, if the response time is longer than the standard time, a degree of darkening the luminance of the stimulus is restricted in comparison with a case where the response time is shorter than the standard time, so that the measurement accuracy can be improved.

Another aspect of the invention is the ophthalmic testing unit, wherein said stimulus presentation portion is comprised of a projection optical system for projecting said stimulus and a projection member on which said stimulus is projected by said projection optical system.

According to this aspect of the invention, a visual field of an examinee is judged by not only simple judgment of the result of an examinee's perception of stimulus, but also by a time for perceiving stimulus (that is, the response time), so that the measurement accuracy can be improved.

BRIEF DESCRIPTION OF THE DRAWINGS

FIG. 2 is a table for explaining an illustrative method of testing a visual acuity;

FIG. 12(*a*) is a typical view showing an illustrative screen of the monitor to be displayed during execution of program for measuring a rod, FIG. 12(*b*) is a typical view showing an illustrative screen of the monitor to be displayed during execution of program for measuring a cone, and FIG. 12(*c*) is a typical view showing an illustrative screen of the monitor to be displayed when finishing the program for measuring the rod and the program for measuring the cone;

BEST MODE FOR CARRYING OUT THE INVENTION

The invention has optotype presentation means for presenting optotypes to an examinee, operation means to be operated by the examinee, for outputting a result of perception of the optotype by the examinee as a signal, response time measuring means for measuring a response time from presentation of the optotype by the optotype presentation means till output of a signal by the operation means, standard time output means for outputting a standard time with respect to the response time, time comparison means for comparing a result of measurement by the response time measuring means and the standard time which is outputted from the standard time output means, and optotype change means for changing the optotype which is presented by the optotype presentation means into one which is harder to be perceived for the examinee if the time comparison means judges the response time to be shorter than the standard time.

According to the invention, accurate testing of a visual acuity is possible, taking a response time into consideration. A visual acuity testing device and a visual field device will now be explained hereinafter in detail.

Figure 1:
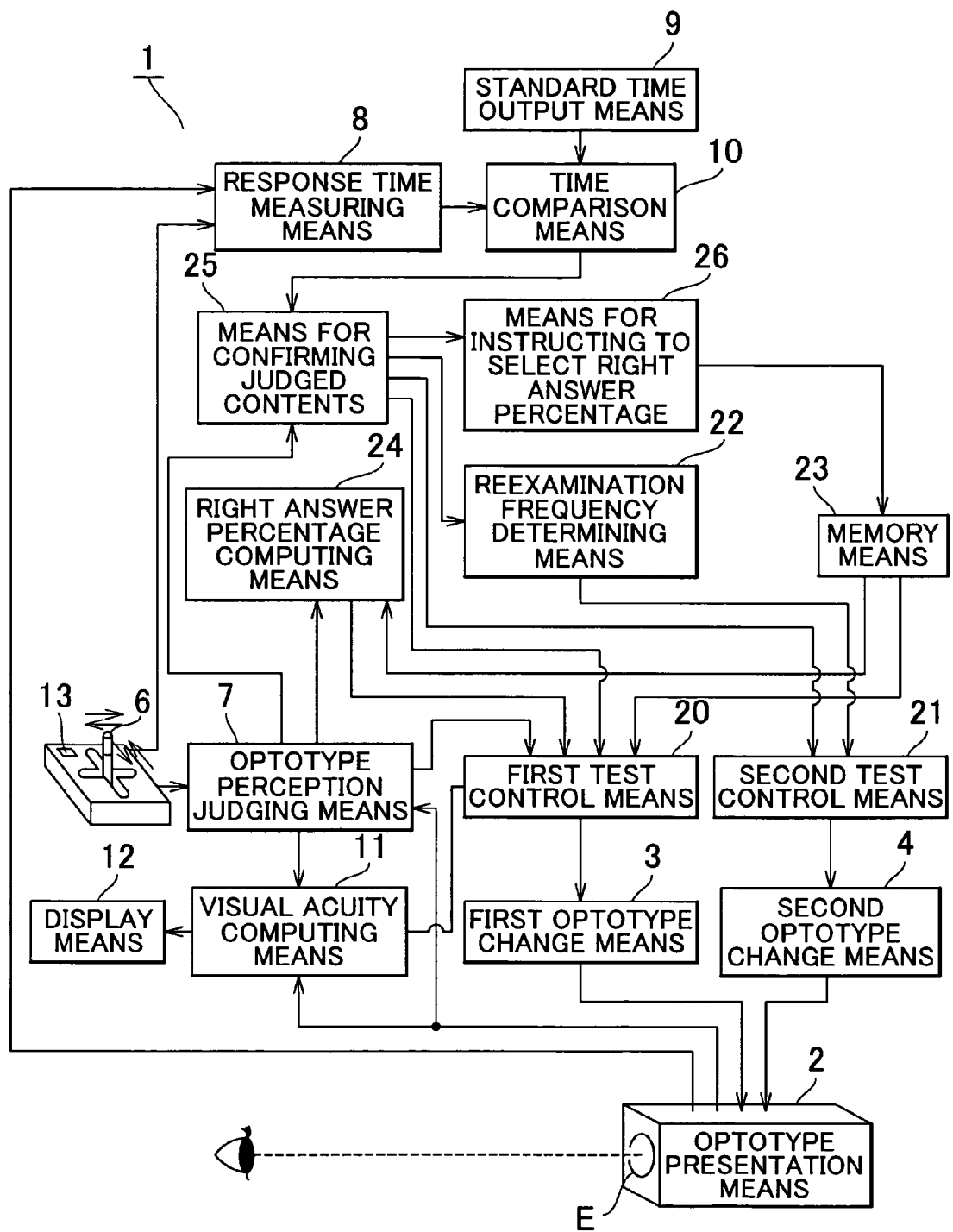
FIG. 1 is a block diagram showing a structure of a visual acuity testing device according to the invention.

A visual acuity testing device which is shown with a reference numeral 1 in FIG. 1 according to the invention has an optotype presentation means 2 for presenting optotype E to an examinee, a first optotype change means 3 for changing the optotype E to be shown by the optotype presentation means 2 into smaller one, a second optotype change means 4 for changing the optotype E to be shown by the optotype presentation means 2 into one having the same size and the other shape, a first test control means 20 for driving the first optotype change means 3, and a second test control means 21 for driving the second optotype change means 4.

And, the visual acuity testing device 1 according to the invention has an operation means 6 to be operated by examinees for outputting judgment results of perception of optotypes by an examinee as signals, and an optotype perception judging means 7 for judging a right/wrong answer of perception of the optotype by an examinee by comparing a signal outputted from the operation means 6 and a signal from the optotype presentation means 2, so that it can automatically judge a right/wrong answer of perception of the optotype. Therefore, a visual acuity can be examined with only operation of the operation means 6 by an examinee, so that works and time for the visual acuity examination can be decreased without taking such a style that a tester invites an examinee to respond, operating the device and then, the examinee answers.

And, the visual acuity testing device 1 according to the invention has a response time measuring means 8 for measuring a response time from first presentation of optotype E by the optotype presentation means 2 to output of a signal by the operating means 6, standard time output means 9 for outputting a standard time on the response time, and time comparison means 10 for comparing result measured by the response time measuring means 8 with the standard time outputted by the standard time output means 9.

The first test control means 20 can test a higher visual acuity by driving the first optotype change means 3 if the optotype perception judging means 7 judges a result of first perception of the optotype to be right and at the same time, the time comparison means 10 judges the response time to be smaller than the standard time (see A of FIG. 2). And, the second test control means 21 can test the same visual acuity grade again by driving the second optotype change means 4 if either the judgment of the first perception of the optotype to be right or the judgment of the response time to be smaller than the standard time is lacked (see B through D of FIG. 2). According to the invention, the same visual acuity grade is controlled to be tested again if the response time is too long or the result of the perception of the optotypes is wrong, so that the accuracy of visual acuity test can be improved in comparison with the test having no such reinspection. If an examinee can not immediately perceive too small optotypes and responds after taking a longer time, hesitating to respond, for instance, the test is executed again even if the result of the perception of the optotypes is right, so that the accuracy of the visual acuity test can be improved. And, the test is executed again if an examinee makes a wrong answer due to an operation error of the operation means 6 although the examinee completely perceives the optotypes, so that the accuracy of the visual acuity test can be improved. On the contrary, time for examination can be shortened by the time for reexamination if the response time is shorter and the result of the perception of the optotypes is right since no reexamination does not almost lead to deterioration of testing accuracy.

It is preferable to provide reexamination frequency determining means 22 for determining the maximum number of times to be executed of reexamination of the same visual acuity grade, memory means for storing standard right answer percentages on the right answer percentage at the time of reexamination, and right answer percentage computing means 24 for computing the right answer percentage at the time of the reexamination. Preferably, the second test control means 21 makes a reexamination, and the first test control means 20 drives the first optotype change means 3 so as to test the higher visual acuity grade if the right answer percentage computed by the right answer percentage computing means 24 is higher than the standard right answer percentage which is stored in the memory means 23 at the time of the reexamination (see B through D of FIG. 2). In such a case, an examinee can gradually receive examination of a higher visual acuity grade even if the examinee can perceive the optotypes either at the time of first presentation of the optotypes or at the time of reexamination. Then, the highest visual acuity grade of an examinee can be obtained by repeating such examinations. Although the reexamination frequency determining means 22 determines the maximum number of times of the reexamination, it is not always to make the reexaminations the maximum number of times. This is because the reexamination is stopped before reaching the maximum number of times if the right answer percentage which is computed by the right answer percentage computing means 24 is higher than the standard right answer percentage which is stored in the memory means 23.

Preferably, the memory means 23 stores a) a first standard right answer percentage to be applied when obtaining both judgments, the judgment of the result of first perception of the optotypes to be right and the judgment of the response time to be longer than the standard time, b) a second standard right answer percentage to be applied when obtaining both judgments, the judgment of the result of first perception of the optotypes to be wrong and the judgment of the response time to be shorter than the standard time, and c) a third standard right answer percentage higher than the first standard right answer percentage to be applied when obtaining both judgments, the judgment of the result of first perception of the optotypes to be wrong and the judgment of the response time to be longer than the standard time, and it is preferable to provide means for confirming judged contents 25, which confirms contents of judgment by the optotype perception judging means 7 and contents of judgment of the time comparison means 10, and to provide means for instructing to select right answer percentage 26 which selectively reads the first through third standard right answer percentages out of the memory means 23 according to the result of the confirmation by the means for confirming judged contents 25. Preferably, the first test control means 20 drives the first optotype change means 3 so as to examine the higher visual acuity grade if the right answer percentage which was computed by the right answer percentage computing means 24 is higher than the standard right answer percentage which was read out of the means for instructing to select right answer percentage 26. Then, more proper visual acuity examination is possible since the standard right answer percentage is switched according to the results of the first perception of the optotypes.

In case of B as shown in FIG. 2, the maximum number of time for reexamination is twice, "a second presentation of optotypes" and "a third presentation of optotypes", and in case of C, it is once, and in case of D, it is twice. The first standard right answer percentage is 50 percent (see B of FIG. 2), the second standard right answer percentage is 100 percent (see C of FIG. 2), and the third standard right answer percentage is 100 percent (see D of FIG. 2). In other words, giving right answer in either first or second reexamination leads to examination at the higher visual acuity grade in case of B in FIG. 2. And, giving right answer in only first reexamination leads to examination at the higher visual acuity grade in case of C in FIG. 2, and giving right answer in both reexaminations leas to examination at the higher visual acuity grade in case of D.

Although the response time passes the standard time in the above-mentioned both a) and c), a person of a) who gave a right answer on the first perception of optotype is thought to have the visual acuity higher than a person of c) who did not give a right answer with relatively higher possibility. With such a situation, the person of a) can receive "an examination at the higher visual acuity grade" even if the right answer percentage at the time of reexamination is lower than the person of c). In such a case, low standard right answer percentage at the time of reexamination does not lead to deterioration of the examination accuracy.

Preferably, the reexamination frequency determining means 22 executes the reexamination at the same visual acuity grade only once when obtaining both judgments by the means for confirming judged contents 25, the judgment of the first perception result of the optotype to be wrong, and the judgment of the response time to be shorter than the standard time, and the memory means 23 outputs a value of 100 percent as the second standard right answer percentage, and the first test control means 20 drives the first optotype change means 3 so as to execute the examination at the higher visual acuity grade if right answer is given in one reexamination (see C of FIG. 2). In a case where an examinee who is unfamiliar with an operation of the operation means 6 inadvertently makes error operation of the operation means 6 although the examinee completely perceives the optotypes, the response time is short and the result of perception of optotypes is wrong in many cases. In such a case, one time reexamination does not lead to the deterioration of the examination accuracy, and the examination time can be shortened with small number of times of reexamination.

In FIG. 2, the upper limit on the number of times to be examined at the same visual acuity grade is three times, but may be four or more times. Besides, the standard right answer percentage in the second and third presentation of the optotypes is 50 percent in case B and 100 percent in case D, but these numeral values are not limiting.

Figure 3:
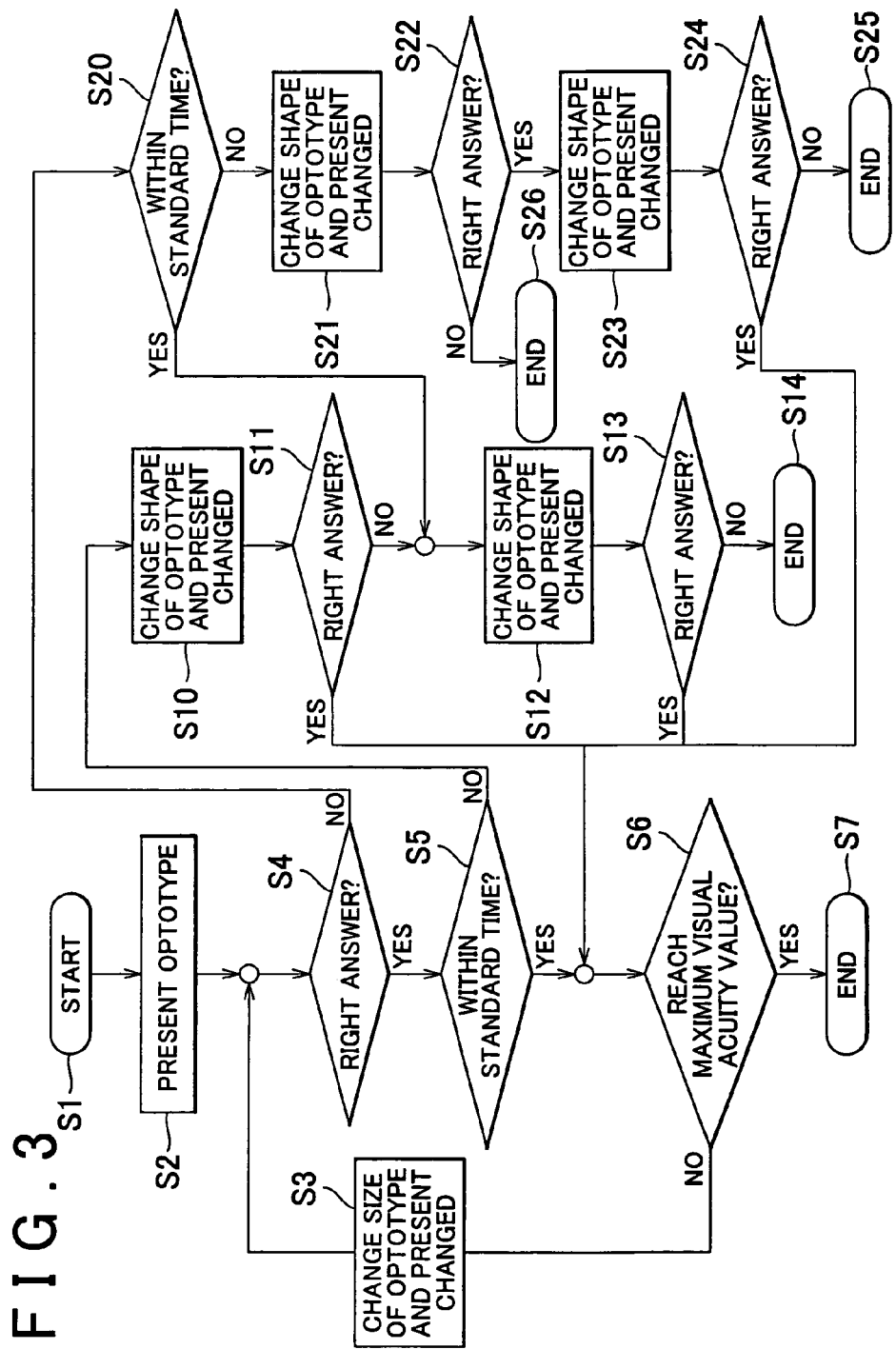
FIG. 3 is a flow chart showing an illustrative method of testing a visual acuity.

A method of testing visual acuity with the unit as shown in FIG. 1 is now explained, referring to FIG. 3.

When starting a visual acuity testing program while an examinee faces the visual acuity testing device 1 (see S1), the optotype presentation means 2 lets an examinee see optotypes E (S2) and the response time measuring means 8 starts to measure time. An examinee may not know this measurement of time.

If an examinee inputs the result of perception of the optotypes through the operation means 6 in the afore-mentioned state, the optotype perception judging means 7 judges the examinee's perception of the optotypes by comparing a signal outputted from the operating means 6 and a signal from the optotype presentation means 2. When obtaining both judgments, a judgment of the result of the first perception of the optotypes to be right by the optotype perception judging means 7 and a judgment of the response time to be shorter than the standard time by the time comparison means 10 (S4 and S5), the first test control means 20 drives the first optotype change means 3 so as to test the higher visual acuity grade (S3). Then, the optotypes become smaller every right answer by an examinee within the standard time until the visual acuity test finishes at the highest visual acuity grade (S6 and S7). Whether or not the visual acuity of an examinee reaches the highest grade is judged when obtaining a predetermined right answer percentage in a reexamination, in addition to the above-mentioned case.

Even if the optotype perception judging means 7 judges the result of a first perception of optotypes to be right (S4), the second test control means 21 drives the second optotype change means 4 so as to examine the same visual acuity grade (S10) when the response time is longer than the standard time (S5). And, the first optotype change means 3 is controlled to be driven so as to test the higher visual acuity grade (S3) in the way similar to the above-mentioned when giving a right answer at a first reexamination (S11) or giving a wrong answer in a first reexamination but a right answer in a second reexamination (S11 through S13). The visual acuity test finishes in case of a wrong answer in both reexaminations (S14).

If the result of the first perception of optotypes is wrong (S4) and the response time is shorter than the standard time (S20), the second test control means 21 drives the second optotype change means 4 and test the same visual acuity grade only once (S12). If the right answer is given in the reexamination (S13), the first optotype change means 3 is driven so as to test the higher visual acuity grade in the similar way (S3). If a wrong answer is given, the visual acuity test finishes (S14).

If the result of the first perception of optotypes is wrong (S4) and the response time is longer than the standard time (S20), the second test control means 21 drives the second optotype change means 4 so as to test the same visual acuity grade in a reexamination (S21, S23) If a right answer is given in both reexaminations (S21 through S24), the first optotype change means 3 is driven so as to test the higher visual acuity grade (S3). If a wrong answer is given in both reexaminations, the visual acuity test finishes (S25 and S26).

Preferably, the optotype presentation means 2 is means for showing Landolt ring optotypes E to an examinee. In such a case, preferably, the first optotype change means 3 changes the shown Landolt ring optotypes into smaller ones, and the second optotype change means 4 changes the shown Landolt ring optotypes into ones each having the same size and changed position of a slit. For instance, a slit is preferably changed into any of up, down, right and left.

Preferably, the operation means 6 is a lever typed switch or a push button. When an examinee is invited to answer a position of a slit of the optotype E which is a Landolt ring, it is preferable to use a joystick lever (see FIG. 1) which can be inclined to up, down, right or left or four push button switches which are located at up, down, right and left. Besides, a measurement start switch 13 for instructing a start of a visual acuity test may be located in addition to the operation means 6.

Preferably, the optotype perception judging means 7 is connected with a visual acuity computing means 11 so as to compute the visual acuity of an examinee according to a signal from the optotype presentation means 2 and a signal from the optotype perception judging means 7, as shown in FIG. 1. Preferably, the visual acuity is computed before or after driving the first optotype change means 3 by the first test control means 20 so as to test the higher visual acuity grade. In such a case, the visual acuity computing means 11 automatically computes the visual acuity with no manual operation, so that time and works for the visual acuity test can be decreased and computing errors can be avoided. Preferably, display means 12, such as a printer and a monitor, is connected with the visual acuity computing means 11 so as to display the computed visual acuity grade.

Figure 4:
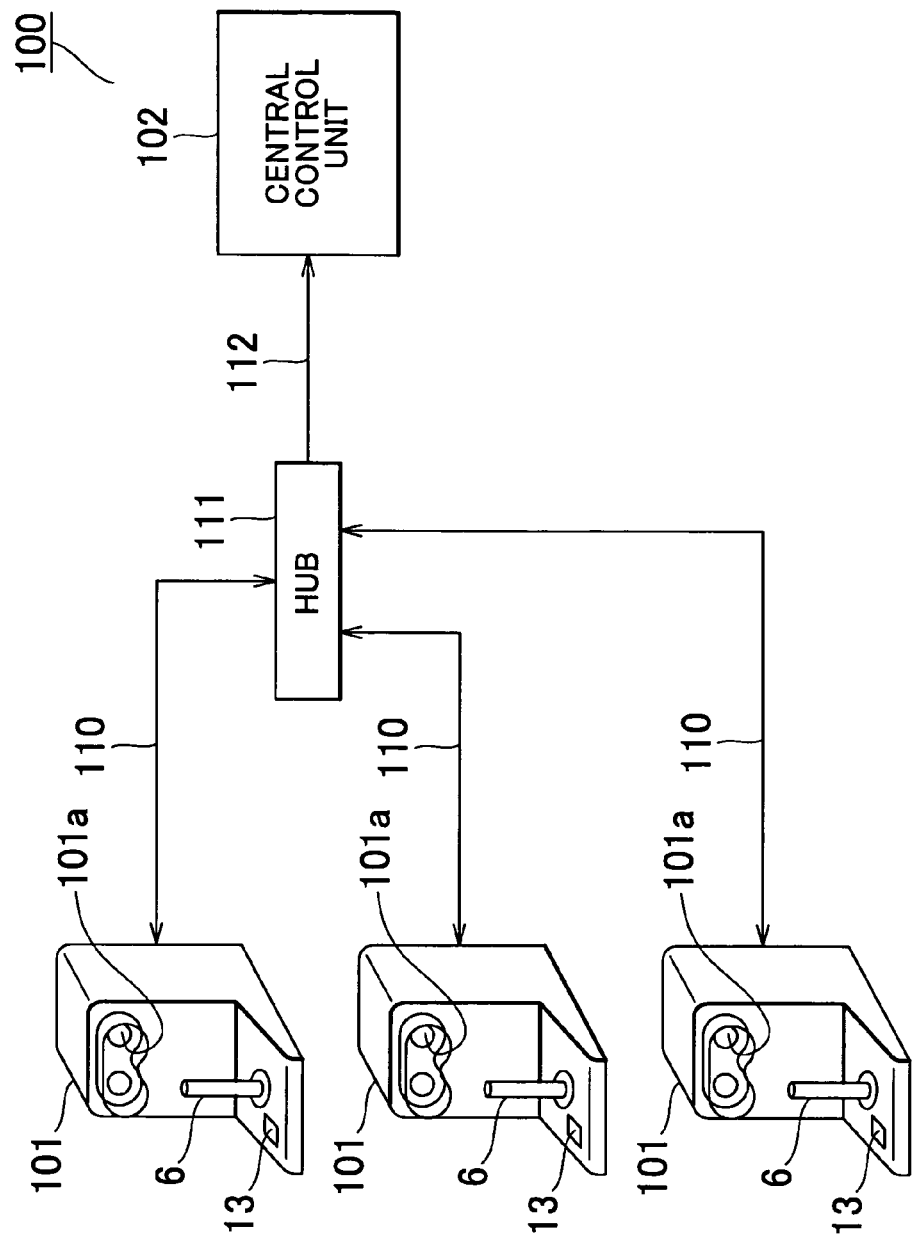
FIG. 4 is a typical view showing the whole structure of a visual acuity testing equipment having a central control unit for unitarily controlling a plurality of the visual acuity testing devices.
Figure 5:
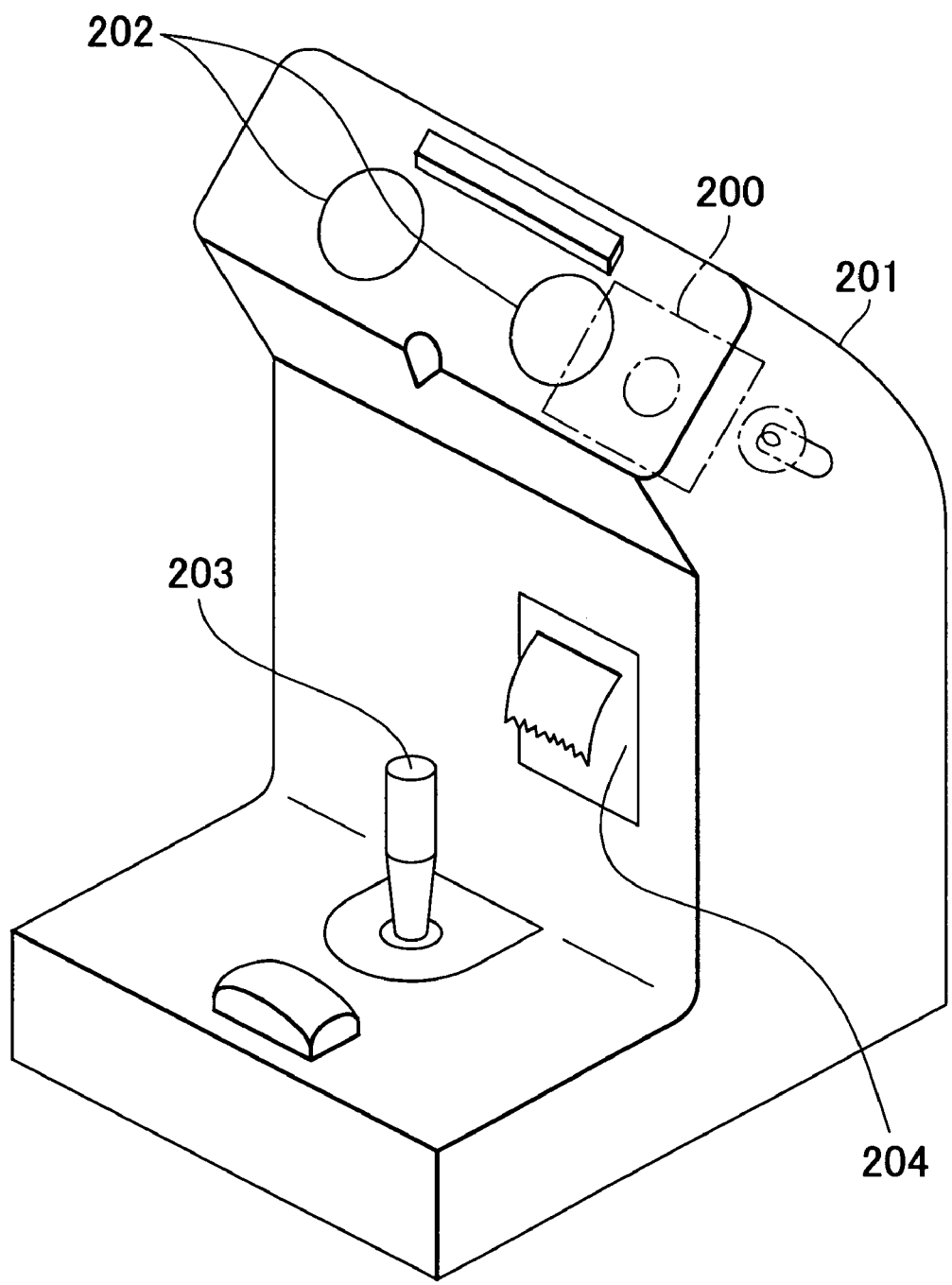
FIG. 5 is a perspective view showing appearances of a structure of a conventional automatic visual acuity testing device.

Preferably, a visual acuity testing equipment 100 is comprised of two or more visual acuity testing devices 101 and a central control unit 102 which is connected therewith, as shown in FIG. 4. Each visual acuity testing device 101 has at least optotype presentation means for showing the optotypes E to an examinee (see reference numeral 2 of FIG. 1) and the operation means 6 for outputting the result of perception of optotypes of an examinee through an operation of the examinee as a signal. Preferably, at least one of the visual acuity testing device 101 and the central control unit 102 has optotype perception judging means for judging the perception of optotypes by an examinee according to a comparison between signals from the optotype presentation means 2 and the operation means 6 (see reference numeral 7 of FIG. 1)

response time measuring means for measuring a response time from first presentation of optotype by the optotype presentation means 2 to output of a signal by the operating means 6 (reference numeral 8 of FIG. 1)

standard time output means for outputting a standard time on the response time (reference numeral 9 of FIG. 1)

time comparison means for comparing the result measured by the response time measuring means 8 and the standard time outputted by the standard time output means 9 with each other (reference numeral 10 of FIG. 1)

first optotype change means for changing the optotype E to be presented by the optotype presentation means 2 into a smaller one (reference numeral 3 of FIG. 1)

second optotype change means for changing the optotype E to be presented by the optotype presentation means 2 into one having the same size and a different shape (reference numeral 4 of FIG. 1)

first test control means for driving the first optotype change means 3 so as to test the higher visual acuity grade when obtaining both judgments, a judgment of the result of a first perception of optotypes to be right by the optotype perception judging means 7 and a judgment of the response time to be shorter than the standard time by the time comparison means 10 (reference numeral 20 of FIG. 1), and second test control means for driving the second optotype change means 4 so as to test the same visual acuity grade when not obtaining at least one of both judgments, a judgment of the result of a first perception of optotypes to be right by the optotype perception judging means 7 and a judgment of the response time to be shorter than the standard time by the time comparison means 10 (reference numeral 21 of FIG. 1).

According to the visual acuity testing equipment 100, an operator can unitarily control visual acuity tests to be executed by two or more visual acuity testing devices 101 with the central control unit 102, so that works or time for the visual acuity test can be decreased. Preferably, each visual acuity testing device 101 is connected with the central control unit 102 through a communication line 110, a hub 111 and a communication line 112. A reference numeral 101a of FIG. 4 denotes a test window for looking into optotypes.

A visual field device which is another embodiment of the ophthalmic testing unit according to the invention will now be explained hereinafter.

Figure 6:
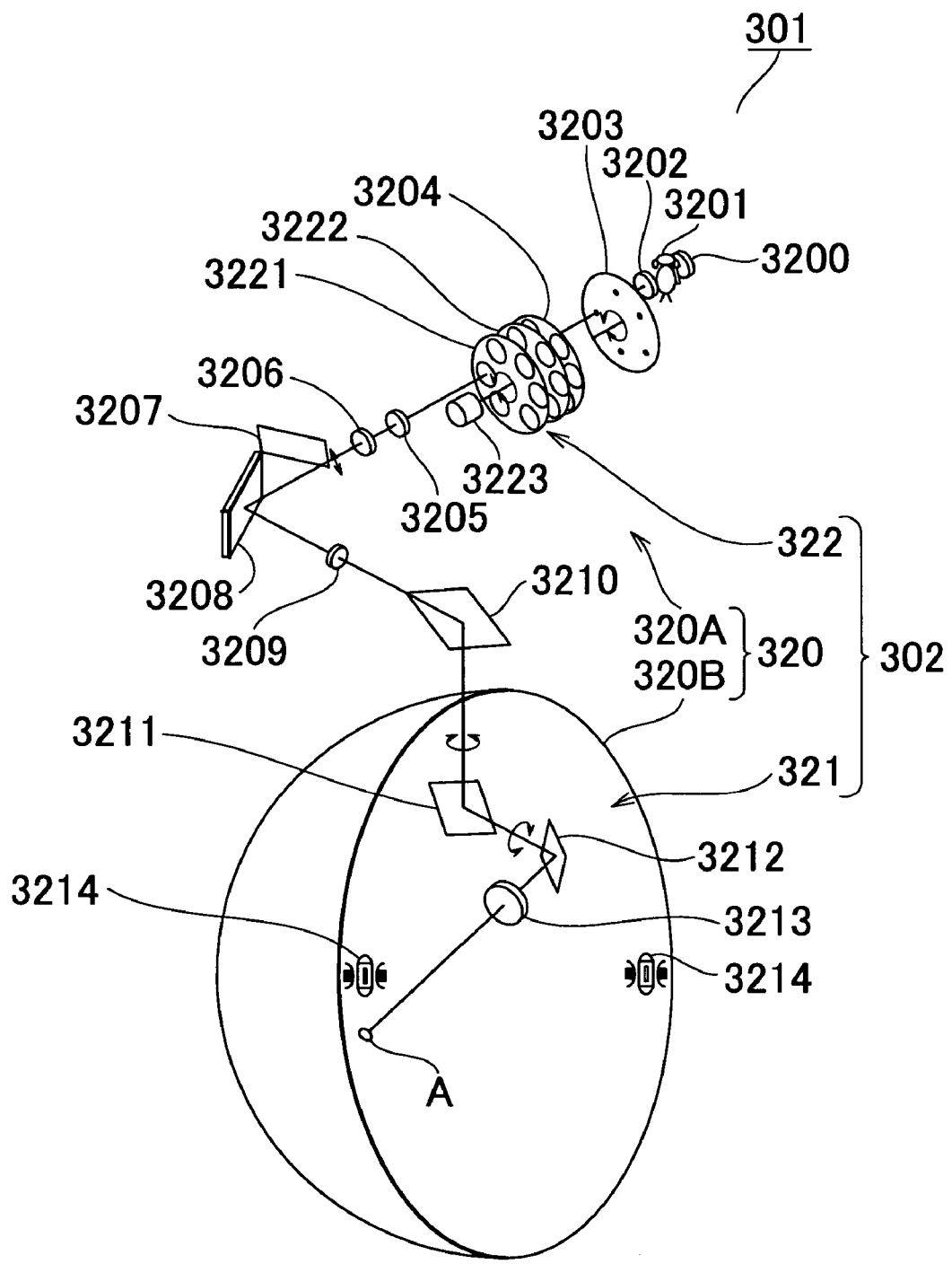
FIG. 6 is a typical view showing a structure of a visual field device according to the invention.

The visual field device according to the invention is a reference numeral 301 of FIG. 6, for instance, and has a stimulus display means 302 which is comprised of a stimulus presentation portion 320 for presenting stimuli A inside a visual field of an examinee, a position change portion 321 for changing a position to be displayed of the stimulus A, and a luminance setting portion 322 for setting a luminance of the stimulus A so as to successively display the stimuli A having predetermined luminances at various positions in the visual field of an examinee.

The stimulus presentation portion 320 of FIG. 6 is comprised of a projection optical system 320A for projecting stimuli and a projection member 320B on which stimuli are projected, but may have any structure as long as it can present stimuli in the visual field of an examinee. For instance, a plurality of LEDs may be arranged, and these may selectively light. The projection member 320B of FIG. 6 is semi-sphere dome, but may have a curved surface excluding a semi-sphere or a planar shape.

In a case where the stimulus presentation portion 320 is comprised of the projection optical system 320A and the projection member 320B as shown in FIG. 6, the position change portion 321 may be driving means (not shown) for changing a position of a component (such as projector mirrors 3211, 3212) of the projection optical system 320A. In a case where the stimulus presentation portion is comprised of a plurality of LEDs, on the other hand, the position change portion may control which LED lights. In any case with the projection optical system or LEDs, change of a position to be displayed may be instructed manually by a tester with a touch pen, a mouse or a keyboard while watching a display during an examination, or may be automatically instructed with a program prepared in advance.

Various types of luminance setting portions 322 are considered to be used. In FIG. 6, the luminance setting portion 322 is comprised of turrets 3221, 3222 to be rotatably supported, each having two or more filters which have different attenuances, and a driving mechanism 3223 for changing positions of the turrets 3221, 3222, and a luminance control portion for controlling the driving mechanism 3223 (a reference numeral 3224 of FIG. 7).

Figure 7:
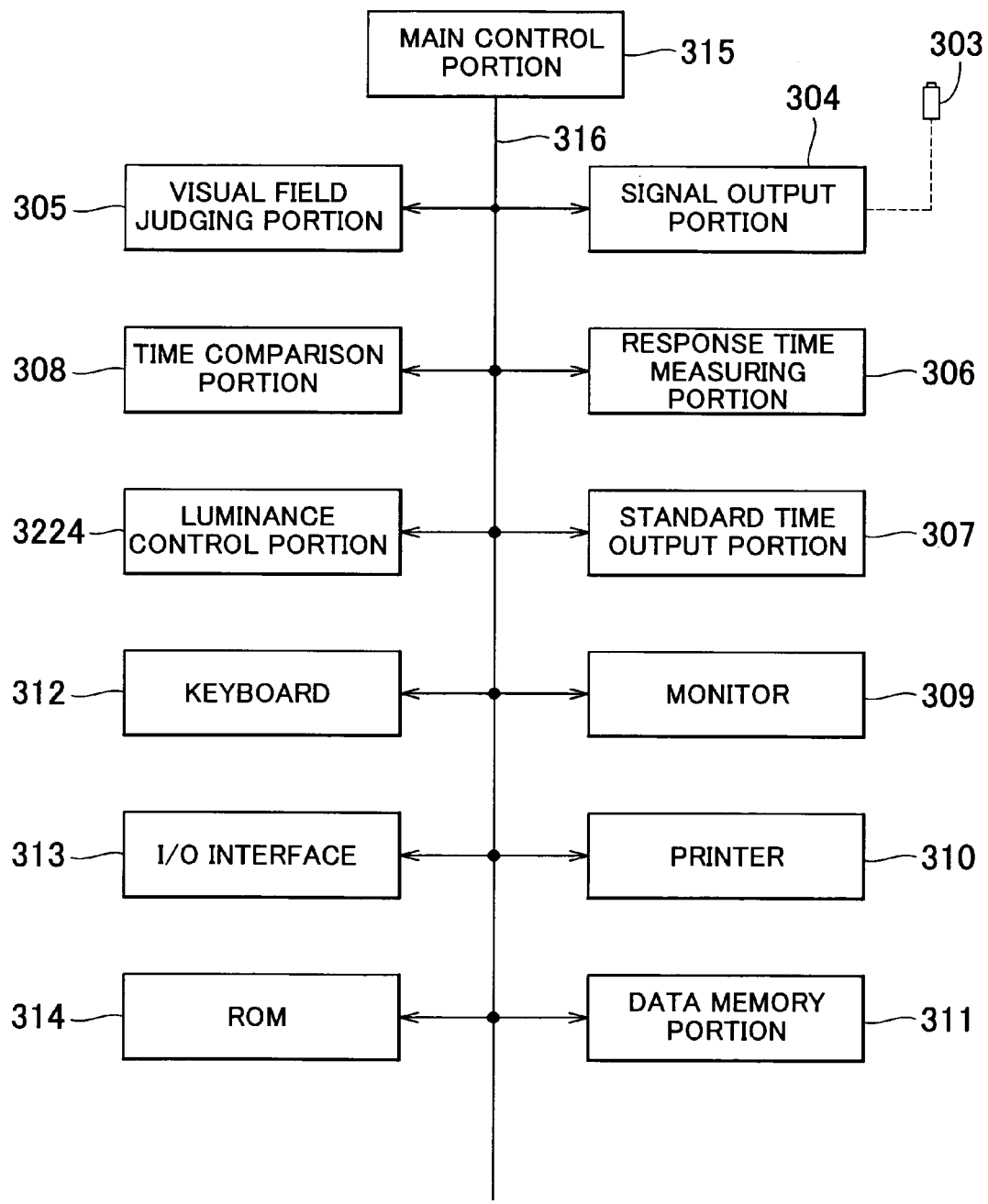
FIG. 7 is a block diagram showing a structure of a control unit to be used for the visual field device according to the invention.

And, as shown in FIG. 7, the visual field device 301 according to the invention has an operation means 303 to be operated by an examinee who perceives displayed stimuli A, a signal output portion 304 for outputting a signal when the operation means 303 being operated, and a visual field judging portion 305 for judging a visual field of an examinee from a position where the stimulus is displayed by the stimulus display means 302 when a signal being outputted by the signal output portion 304 so as to measure the visual field of an examinee.

Besides, the visual field device 301 according to the invention has a response time measuring portion 306 for measuring a response time from display of stimuli by the stimulus display means 302 until output of a signal by the signal output portion 304, a standard time output portion 307 for outputting a standard time which is a base judgment as to whether or not luminance of the stimulus A should be changed by the luminance setting portion 322, and a time comparison portion 308 for comparing the response time and the standard time with each other. The luminance setting portion 322 is means for darkening the luminance of the stimulus by a first predetermined volume if the time comparison portion 308 judges the response time to be shorter than the standard time, and for darkening the luminance of the stimulus by a second predetermined volume if the time comparison portion 308 judges the response time to be longer than the standard time. Preferably, the first predetermined volume is more than the second predetermined volume in such a case. According to the invention, a visual field of an examinee is judged by not only simple judgment of the result of an examinee's perception of stimuli, but also by a time for perceiving stimuli (that is, the response time), so that the measurement accuracy can be improved.

As shown in FIG. 7, a main control portion 315 is arranged in the visual field device according to the invention. Preferably, the signal output portion 304, the visual field judging portion 305, the response time measuring portion 306, the standard time output portion 307, the time comparison portion 308, a luminance control portion 3224, a monitor 309, a printer 310, a data memory portion 311, a keyboard 312, an I/O interface 313 and a ROM 314 are connected with the main control portion 315 via a bus line 316.

A method of measuring a visual field according to the invention will now be explained, referring to FIG. 8 through FIG. 13.

Figure 8:
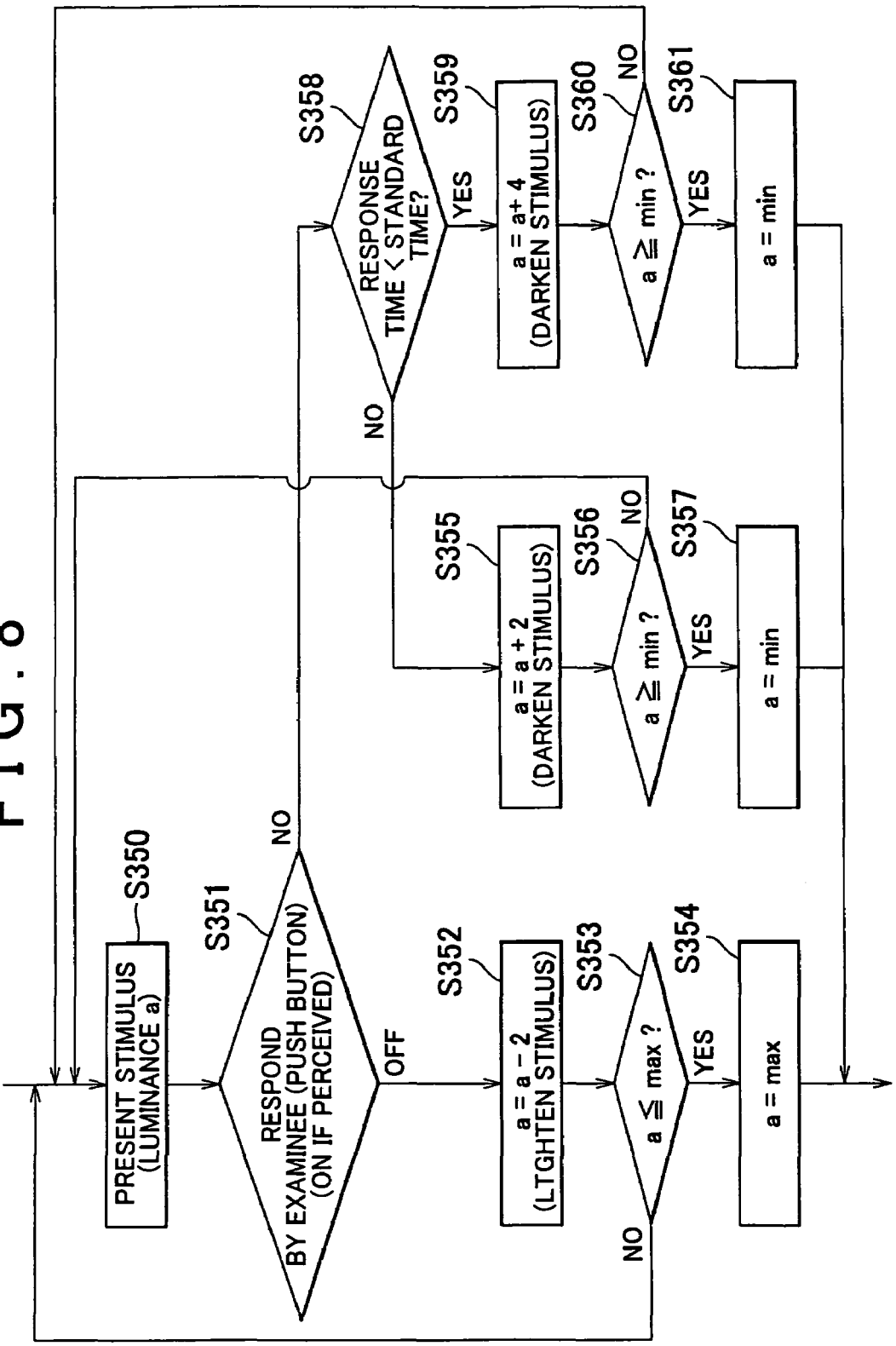
FIG. 8 is a flow chart showing an illustrative method of measuring a visual field.

When starting the visual field device 301 according to the invention while an examinee is fixating a specific fixation point, the stimulus presentation portion 320 presents the stimulus A having a predetermined luminance at a predetermined position in a visual field of the examinee (see S350 of FIG. 8). At this time, the position change portion 321 sets a position of the stimulus to be displayed and the luminance setting portion 322 sets a luminance of the stimulus.

Figure 13:
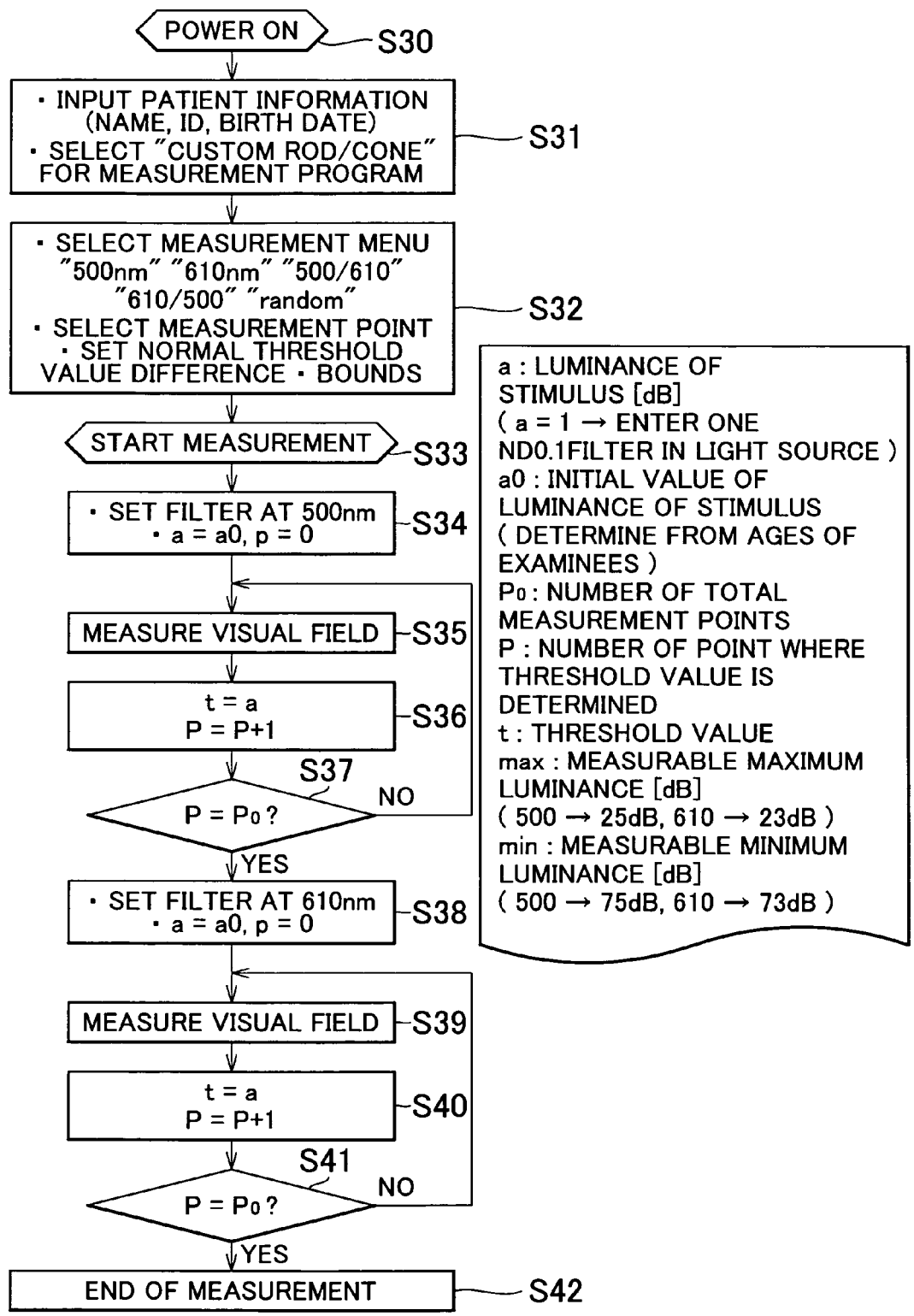
FIG. 13 is a flow chart showing how to execute the program for measuring the rod and the program for measuring the cone.
Figure 14:
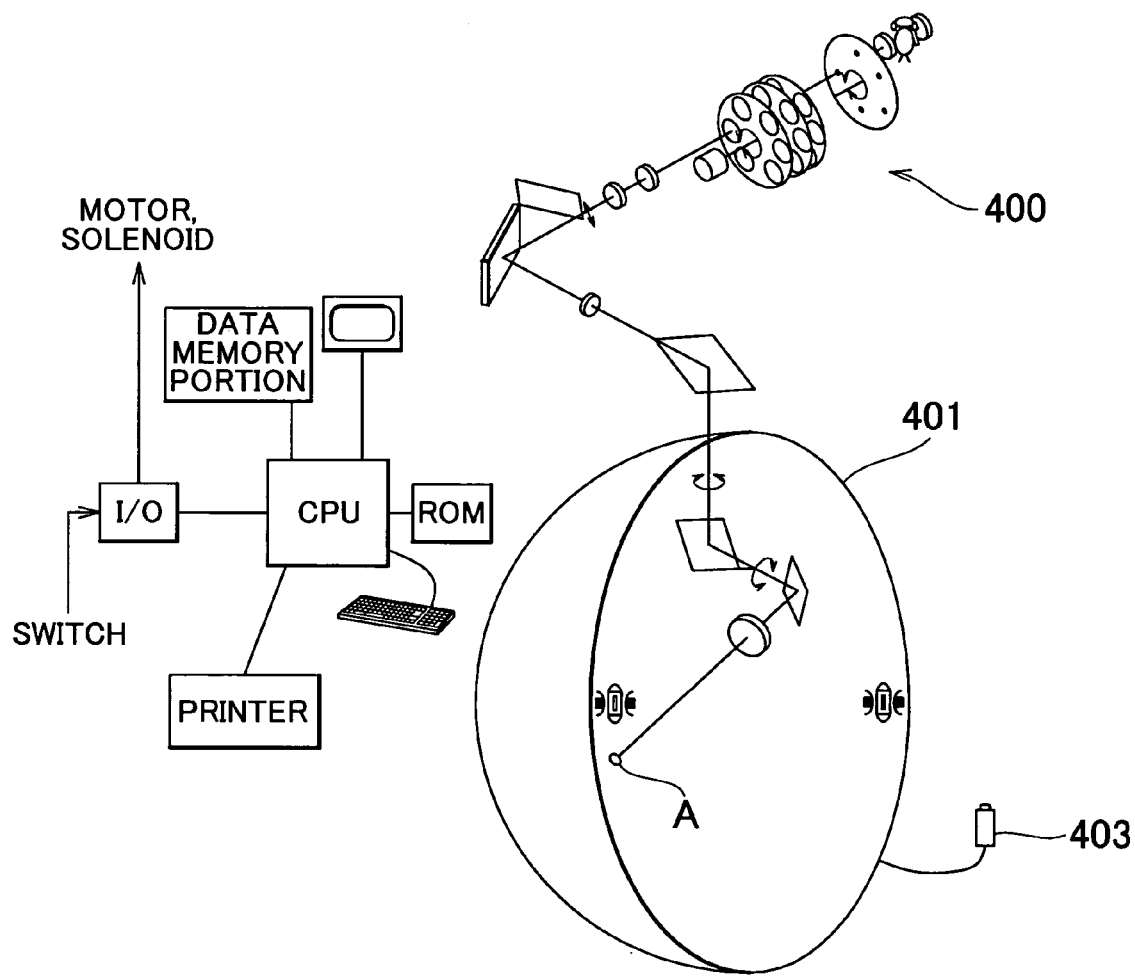
FIG. 14 is a typical view showing a structure of a conventional visual field device.

If no signal is outputted from the signal output portion 304 after passage of a constant time due to no operation of the operation means 303 by an examinee (S351 of FIG. 8), the position of the stimulus to be displayed is changed by the position change portion 321 (S36→S37→S35 of FIG. 13).

If the stimulus can be perceived, an examinee operates the operation means 303. If the operation means 303 is operated (S351 of FIG. 8), the signal output portion 304 outputs a signal and the visual field judging portion 305 judges the visual field of an examinee on the basis of the position of the stimulus displayed by the stimulus display means 302.

When the operation means 303 being operated, the response time measuring portion 306 measures a time from the display of the stimuli by the stimulus display means 302 to output of a signal by the signal output portion 304 (the response time), and the time comparison portion 308 compares the standard time outputted from the standard time output portion 307 and the response time with each other (S358 of FIG. 8). If the time comparison portion 308 judges the response time to be shorter than the standard time, the luminance of the stimulus is darkened by the first predetermined volume. If the time comparison portion 308 judges the response time to be longer than the standard time, the luminance of the stimulus is darkened by the second predetermined volume. The measurement of the visual field is repeated in the above-mentioned same manner.

FIRST EMBODIMENT

In this embodiment, the visual field device 301 is comprised of the stimulus display means 302 as shown in FIG. 6 and a control unit as shown in FIG. 7.

Of both, the stimulus display means 302 is provided with the stimulus presentation portion 320 which is comprised of the projection optical system 320A for projecting the stimuli A and the semi-sphere visual field dome (projection member) 320B on which the stimuli are projected so as to display the stimuli A in the visual field of an examinee.

The projection optical system 320A is comprised of a stimulus projection lump 3201 (halogen lamp) which is a light source, a reflecting mirror 3200 which is arranged at a rear side of the lamp 3201, a condenser lens 3202 which is arranged on a front side of the lamp 3201 for condensing, an aperture 3203 for determining a shape or a size of the stimulus A (will be described later in detail), a color filter turret 3204 for determining a color of the stimulus A (will be described later in detail), a relay lens 3205, a focus lens 3206, a shutter 3207 (will be described later in detail), a mirror 3208, a relay lens 3209, a mirror 3210, a projector mirrors 3211, 3212 (will be described later in detail), and a projector lens 3213. A reference numeral 3214 denotes a background lighting lamp.

The aperture 3203 has various sized hole portions, and can move in a rotational direction and an optical axis, and can properly change the size of the stimulus A which is projected on the visual field dome 320B.

The color filter turret 3204 has a filter A for a rod and a filter B for a cone, and is rotated through a servo motor (not shown).

On an optical path between the color filter turret 3204 and the relay lens 3205, two rotatable ND filter turrets 3221, 3222 are arranged. Each of the ND filter turrets 3221, 3222 has a plurality of filters having different attenuances, so that the luminance of the stimulus can be adjusted at a unit of 1 dB by adjusting rotational positions of the respective ND filter turrets 3221, 3222 so as to change a combination of filters for transmitting a light. In this embodiment, a driving mechanism, such as the servo motor 3223, is connected with the ND filter turrets 3221, 3222, and the luminance control portion (reference numeral 3224 of FIG. 7) controls to drive the driving mechanism so as to adjust the luminance. In this embodiment, the luminance setting portion 322 is comprised of the ND filter turrets 3221, 3222, the driving mechanism, such as the servo motor 3223, and the luminance control portion 3224.

A servo motor (not shown) is connected with the projector mirrors 3211, 3212, and the servo motor is connected with the main control portion 315 through the I/O interface 313 (will be described later in detail), and the servo motor is driven so as to change angles of the respective projector mirrors 3211, 3212 so that the displayed position of the stimulus can be changed. In other words, the projector mirrors 3211, 3212 and the servo motor comprises the position change portion in this embodiment. In this embodiment, eight display positions are programmed in advance, and the position change portion 321 automatically successively changes a displayed position (details will be described later).

The shutter 3207 can be opened and closed by a solenoid (not shown). In case of opened state, the stimulus A is displayed, and in case of closed state, no stimulus is displayed.

A jaw stand (not shown) for putting a jaw of an examinee thereon is arranged at a position facing the visual field dome 320B.

The visual field device 301 is provided with the response switch 303 (operation means) so as to be operated by an examinee who perceives the stimulus A, as shown in FIG. 7. And, the signal output portion 304 is connected with the response switch 303 so as to output a predetermined signal when the response switch 303 is operated.

The visual field device 301 according to the invention is provided with the main control portion 315, and the signal output portion 304 and the luminance control portion 3224 are connected with the main control portion 315 via the bus line 316. In addition, with the main control portion 315, the visual field judging portion 305 for judging a visual field of an examinee from a position where a stimulus is displayed when a signal being outputted from the signal output portion 304, the response time measuring portion 306 for measuring a response time from presentation of the stimulus A till output of a signal from the signal output portion 304, the standard time output portion 307 for outputting a standard time which is a basis of change of luminance, the time comparison portion 308 for comparing the response time and the standard time with each other, a touch-panel type of the monitor 309 for inputting measurement conditions and displaying measured results, the printer 310, the data memory portion 311 (such as a RAM and a hard disc) for storing measured results and the like, the keyboard 312, the I/O interface 313 which is connected with the ND filter turrets 3221, 3222, the servo motor 3223 for driving the projector mirrors 3211, 3212, a solenoid for driving the shutter 3207, the ROM 314 for storing program for measurement.

The luminance control portion 3224 is driven after receiving a signal from the time comparison portion 308. In the concrete, if the response time is judged to be shorter than the standard time by the time comparison portion 308, the luminance control portion 3224 change rotational positions of the ND filter turrets 3221, 3222 so as to darken the luminance of the stimulus A by the first predetermined volume, if the response time is judged to be longer than the standard time by the time comparison portion 308, the luminance control portion 3224 changes rotational positions of the ND filter turrets 3221, 3222 so as to darken the luminance of the stimulus A by the second predetermined volume.

And, the stimulus projection lamp 3201 or the background lighting lamp 324 is connected with the main control portion 315 so as to control lighting of both lamps.

A method of measuring a visual field to be executed in the present embodiment is now explained, referring to FIGS. 8 through 13.

Figure 9:
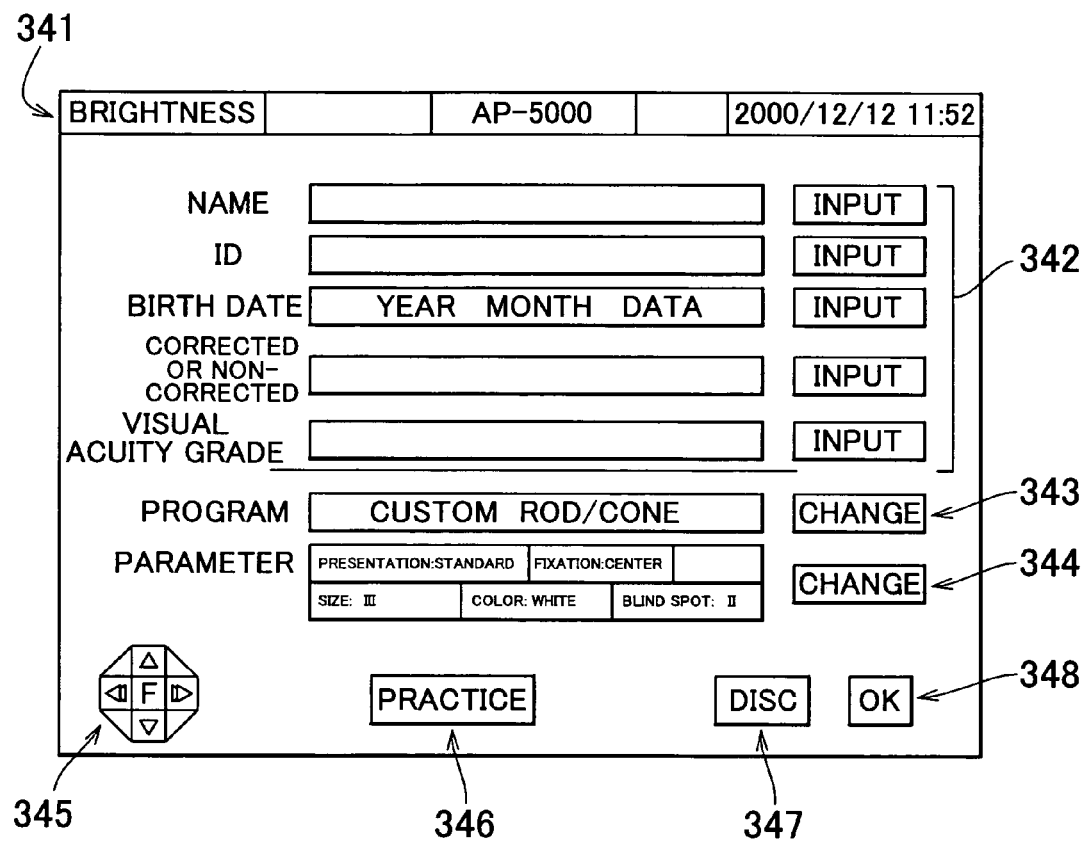
FIG. 9 is a typical view showing an illustrative screen of a monitor for inputting information of an examinee.
Figure 10:
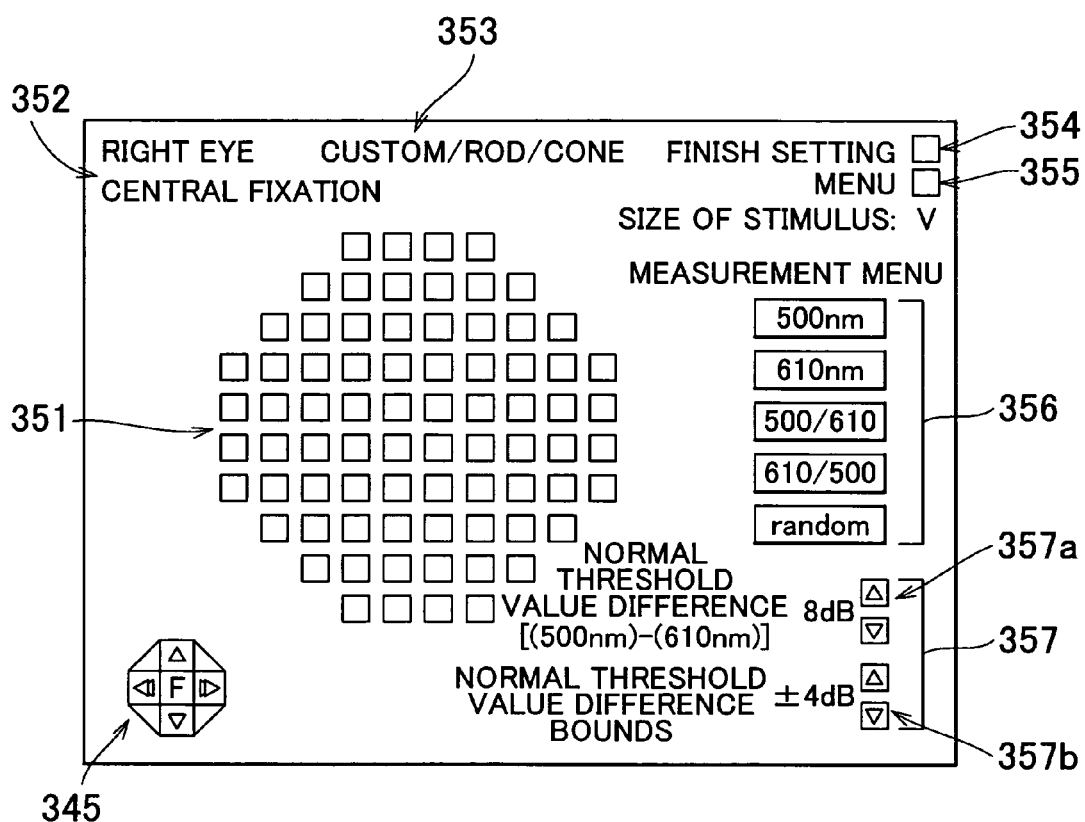
FIG. 10 is a typical view showing an illustrative screen of the monitor for inputting a menu for measurement.

When turning the visual field device on (see S30 of FIG. 13), various buttons (see reference numerals 341 through 347) and an input fields are displayed on the monitor 309, as shown in FIG. 9. Through these buttons 341, . . . and the input fields, information of an examinee (such as information including name, ID, birth date, corrected or uncorrected visual acuity, visual acuity grade of an examinee), program for measurement to be used (program for measuring rod or cone) and parameters (such as sizes and positions of stimuli, and colors) are inputted (see S31 of FIG. 13). A push operation of a OK button 348 which is at a lower portion on the right of a screen after input of all information switches the screen of the monitor 309 into one as shown in FIG. 10.

At a center of the next screen, a lot of squares (see reference numeral 351 of FIG. 10) are arranged, and these squares are buttons for respectively designating displayed positions of the stimuli A in the visual field dome 320B. In a default state of this embodiment, dark eight buttons are selected, and these eight points are measured (details will be described later). Which eye is to be examined and a position of a fixation lamp (not shown) are displayed at a portion of a reference numeral 352, and name of selected program is displayed at a portion of a reference numeral 353.

Buttons 356 are for ones for selecting measurement menu, and the measurement menu of respective buttons in this embodiment is as follows.

First top button: one for measurement of a threshold value of a rod for each measurement point (measurement of threshold value with only 500 nm of filter)

Second button: one for measurement of a threshold value of a cone for each measurement point (measurement of threshold value with only 610 nm of filter)

Third button: measurement menu of default, ones for measurement of a threshold value of a rod for all measurement points and subsequent measurement of a threshold value of a cone for all measurement points Fourth button: ones for measurement of a threshold value of a cone for all measurement points and subsequent measurement of a threshold value of a rod for all points in the order opposite to the third button Fifth button: 500/610 nm of filters are used for each measurement point, but the order of using filters is random, depending on random number generation A button denoted with a reference numeral 357a of FIG. 10 can adjust a normal threshold value difference 1 dB by 1 dB in up or down direction from the default, 8 dB. This normal threshold difference is 8 dB of the threshold value difference to be obtained by both 500 nm and 610 nm color filters when measuring with both filters. A button denoted with a reference numeral 357b can adjust the bounds of upper and lower sides of the normal threshold value difference 8 dB which is judged to be normal (default 4 dB) 1 dB by 1 dB in up/down directions. In the default of this embodiment, a normal bounds is ±4 dB on both upper and lower sides of the normal threshold value difference 8 dB (4 dB through 12 dB).

The measurement menu and the measurement points were thus selected and the normal threshold value difference and the bounds thereof were thus set in the screen of FIG. 10 (S32 of FIG. 13).

Figure 11:
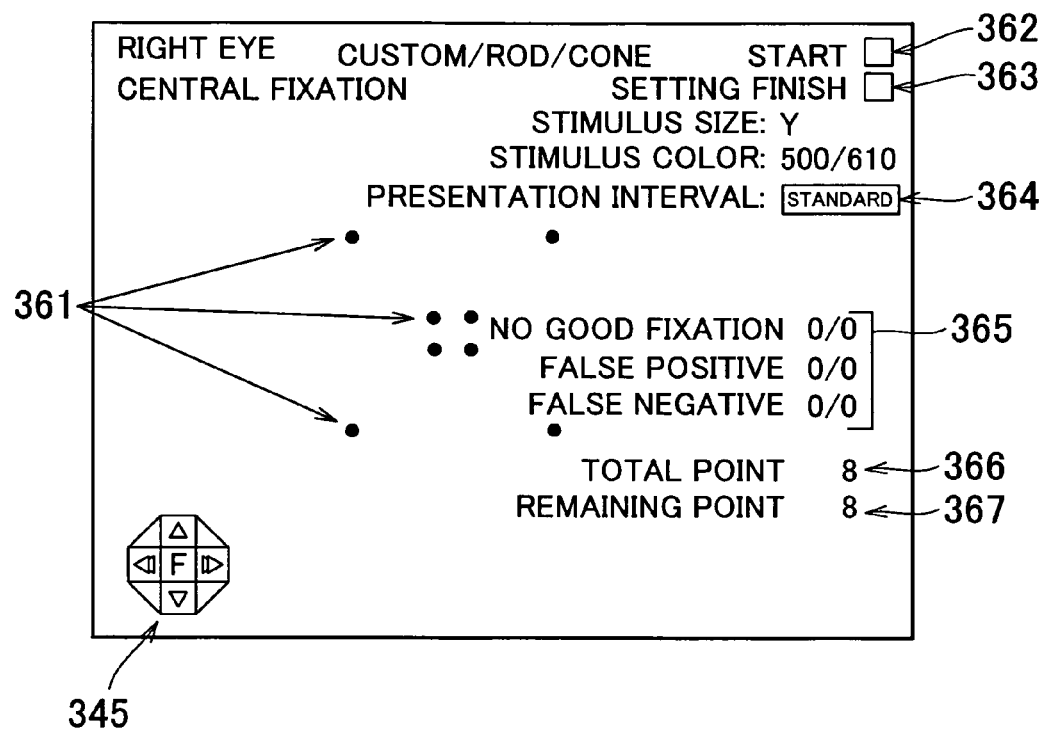
FIG. 11 is a typical view showing an illustrative screen of the monitor to be displayed at a time of measurement start.

When pushing a set finish button 354 on the right upper side of the screen after finish of input of all information, the screen of the monitor 309 is switched into a measurement screen as shown in FIG. 11. The measurement points are displayed with dots as shown in reference numerals 361 on this measurement screen. On the right side of the screen, a start button 362 for instructing a measurement start, a button 363 for instructing return to the set screen, a button 364 for changing an interval of the stimulus displayed are displayed. At a lower portion on the right side of the screen which is denoted with a reference numeral 365, measurement points, such as impossibility of fixation, false positive response and false negative response, are displayed. At a portion dented with a reference numeral 366, total measurement point number is displayed, and at a portion denoted with a reference numeral 367, a number of measurement point for showing that the threshold value has not yet been measured is displayed.

In the afore-mentioned state, an examinee is invited to put one's jaw on a jaw stand (not shown) (then, the right eye of the examinee is positioned at a center of the sphere of the semi-sphere visual field dome 320B) and to fixate a fixation point. Then, the start button 362 on the right upper side of the monitor screen is pushed so as to start measurement (S34 of FIG. 13). In this embodiment, a default value of the measurement menu is selected (that is, the above-mentioned third button), program for measuring a rod is executed for all measurement points (S34 through S37 of FIG. 13), and thereafter, program for measuring a cone is executed for all measurement points (S38 through S41 in FIG. 13). Concrete explanation is as follows.

When pushing the start button 362, the main control portion 315 controls to drive a servo motor (not shown), so that the color filter turret 3204 is rotated so as to set 500 nm of filter. And, the servo motor 3223 is driven through the luminance control portion 3224 so as to set the luminance of stimulus at an initial value a0. Then, a point number p is set at zero (S34 of FIG. 13). A luminance a0 at the time of start of measurement is determined, depending on ages of examinees.

Subsequently, the stimulus projection lamp 3201 or the background lighting lamp 3214 is turned on, the positions of the aperture 3203 and the projector mirrors 3211, 3212 are controlled, the shutter 3207 is opened, and the stimulus A having a predetermined luminance a0 is projected at a predetermined position of the visual field dome 320B (S350 of FIG. 8). If the response switch 303 is not operated for a constant time from presentation of the stimulus A by the projection optical system 320A (S351 of FIG. 8), the main control portion 315 closes the shutter 3207 for stopping display of the stimulus A, and changes the angles of the projector mirrors 3211, 3212, and the servo motor 3223 is driven through the luminance control portion 3224, so that the luminance of the stimulus is lightened by 2 dB from the initial value a0 (S352 of FIG. 8). And, the shutter 3207 is opened and the stimulus is shown (S350 of FIG. 8). Every lightening of the stimulus, as to whether or not the parameter a reaches a measurable maximum luminance max is judged. If reaching the maximum luminance max, the measurable maximum luminance max is set as the parameter a (S353 and S354 of FIG. 8), and the value a is determined as a perceptual threshold value t (S37 of FIG. 13). The same operation is thus repeated for the other measurement points (S37→S35→S36 of FIG. 13).

If an examinee perceives the stimulus A having some luminance, the examinee turns the response switch 303 on (S351 of FIG. 8). Then, the signal output portion 304 outputs a signal, and the visual field judging portion 305 judges the visual field. In the concrete, the angle of the position of the stimulus with respect to the fixation point which is a standard is computed, and the computed result is stored in the data memory portion 311.

If the response switch 303 is turned on, the response time measuring portion 306 measures the response time from presentation of the stimulus till output of a signal from the signal output portion 304, and the time comparison portion 308 compares the standard time (0.5 second in this embodiment) which is outputted from the standard time output portion 307 and the response time (S358 of FIG. 8). If the response time is shorter than the standard time, the stimulus is darkened by 4 dB and is displayed again (S359→S360→S350 of FIG. 8). If the response time is equal to or longer than the standard time, the stimulus is darkened by 2 dB and is displayed again (S355→S356→S350 of FIG. 8). As to whether or not the stimulus luminance value a reaches the minimum luminance min is judged in a process where such an operation is repeated. When reaching the minimum luminance min, the measurable minimum luminance min is set as the parameter a (S357 and S361 of FIG. 8), this value a is determined as the perceptual threshold value t (S37 of FIG. 13). The same operation is thus repeated for the other measurement points (S37→S35→S36 of FIG. 13).

FIG. 12(*a*) is a typical view showing a screen of the monitor which is displayed during execution of the program for measuring a rod. Numerals "61", "61", "60" and "62" which are dispersedly displayed on a center portion of the screen are the threshold values (attenuance of a filter when the response switch 303 responds) of the points on which measurement has already finished. A reference numeral 371 is a point during measurement. And, a mark ☆ which is denoted with a reference numeral 374 is displayed when an examinee operates the response switch 303, and a reference numeral 372 is a push button for instructing interruption of measurement.

The program for measuring a rod finishes when judging that the measurement has been executed for all eight measurement points which are designated in the screen of FIG. 10. Subsequently, the program for measuring a cone starts (S37 through S41 of FIG. 13). In the concrete, the color filter turret 3204 is rotated so as to change the filter into one of 610 nm, the stimulus luminance is set at the initial value a0, and the point number p is set at 0 (S38 of FIG. 13). The measurement of visual field having routines as shown in FIG. 8 is executed again in step S39 of FIG. 13. The measurement finishes after executing the same operations for the other measurement points (S40, S41 and S42 of FIG. 13).

FIG. 12(*b*) is a typical view showing a screen of the monitor which is displayed during execution of the program for measuring a cone. Numerals which are dispersedly displayed in a center of the screen are the threshold values in the respective eight measurement points (attenuance of a filter when the response switch 303 responds). In a point which is shown with only two digits of numeral (a portion at an upper portion on the left side rather than a center which is shown with "62" and a portion on a lower portion on the left side which is shown with "65", and both portions in the center which are shown with "61" and "63"), the measurement of rod has finished, but the measurement of cone has not yet started. This numeral having two digits is the threshold value which is obtained by the measurement of a rod. In points which are respectively shown with numerals having four digits (the points in a center which are shown with "6155" and "6153"

and the point on the upper portion on the right side rather than the center which is shown with "6054" and the point on the lower portion on the right side rather than the center which is shown with "6254"), on the other hand, the first two digits is the threshold value which is obtained by the measurement of rod and the other two digits is the threshold value which is obtained by the measurement of cone.

When finishing both the program for measuring rod and the program for measuring cone, the screen of the monitor 309 is switched into one as shown in FIG. 12(c), for instance, and the measurement results are displayed for all measurement points. A reference numeral 376 denotes a button for instructing reexamination, and a reference numeral 377 denotes a button for instructing output to a printer, and a reference numeral 378 denotes a button for switching the measurement for the other eye, and a reference numeral 379 denotes a button for instructing finish of the measurement.

INDUSTRIAL APPLICABILITY

The invention can be used when measuring a visual acuity and a visual field of an examinee.

The invention claimed is:

1. An ophthalmic testing unit having optotype presentation means for presenting optotypes to an examinee, operation means to be operated by said examinee, for outputting a result of perception of said optotype by said examinee as a signal, and an optotype perception judging means for judging perception of said optotype by said examinee by comparing signals from said optotype presentation means and said operation means with each other, comprising:
  response time measuring means for measuring a response time from presentation of said optotype by said optotype presentation means to output of a signal by said operation means:
  standard time output means for outputting a standard time with respect to said response time;
  time comparison means for comparing a result of measurement by said response time measuring means and said standard time which is outputted from said standard time output means with each other:
  first test control means for actuating when obtaining both judgments, a judgment of a result of said perception of said optotype to be right by said optotype perception judging means and a judgment of said response time to be shorter than said standard time by said time comparison means;
  second test control means for actuating when not obtaining either of said both judgments, said judgment of said result of said perception of said optotype to be right and said judgment of said response time to be shorter than said standard time;
  first optotype change means for changing said optotype which is presented by said optotype presentation means into a smaller one and for starting to clock by said response time measuring means so as to examine a higher visual acuity grade whenever said first test control means is actuated;
  second optotype changing means for changing said optotype which is presented by said optotype presentation means into one having the same size and a different shape so as to retest the same visual acuity grade when said second test control means is actuated;
  reexamination frequency determining means for determining maximum number of times of reexamination at the same visual acuity grade,
  memory means for storing standard right answer percentages on right answer percentage at a time of said reexamination, said standard right answer percentages comprising a) a first standard right answer percentage, b) a second standard right answer percentage and c) a third standard right answer percentage, said first standard right answer percentage being applied when obtaining said both judgments, said judgment of said result of said first perception of said optotype to be right and said judgment of said response time to be longer than said standard time, said second standard right answer percentage being applied when obtaining said both judgments, said judgment of said result of said first perception of said optotype to be wrong and said judgment of said response time to be shorter than said standard time, said third standard right answer percentage being applied when obtaining said both judgments, said judgment of said result of said first perception of said optotype to be wrong and said judgment of said response time to be longer than said standard time;
  right answer percentage computing means for computing an actual right answer percentage at a time of said reexamination;
  judged contents confirming means for confirming contents judged by said optotype perception judging means and contents judged by said time comparison means; and
  right answer selection instructing means for selectively reading said first through third standard right answer percentages out of said memory means according to a result confirmed by said judged contents confirming means,
  wherein said first test control means drives said first optotype change means so as to examine a higher visual acuity grade if said right answer percentage computed by said right answer computing means is higher than said standard right answer percentage read out of said memory means by said right answer percentage selection instructing means.

2. The ophthalmic testing unit according to claim 1, wherein said reexamination frequency determining means executes a reexamination at the same visual acuity grade only once if said judged contents confirming means judges said result of said first perception of said optotype to be wrong and said response time to be shorter than said standard time, and said memory means outputs 100 percent as said second standard right answer percentage, and said first test control means drives said first optotype change means so as to examine a higher visual acuity grade if a right answer is given at said reexamination executed once.

3. An ophthalmic testing unit for measuring a visual field of an examinee by successively displaying stimuli having predetermined luminances at various positions in said visual field of said examinee, comprising:
  stimulus display means being comprised of an stimulus presentation portion for presenting said stimulus in said visual field of said exarninee, a displayed position change portion for changing a displayed position of said stimulus, and a luminance setting portion for setting said luminance of said stimulus;
  operation means to be operated by said examinee who have perceived said stimulus displayed;
  a signal output portion for outputting a signal when said operation means being operated;
  a visual field judging portion for judging said visual field of said examinee when said signal being outputted from said signal output portion;

a response time measuring portion for measuring a response time from presentation of said stimulus by said stimulus display means to output of said signal from said signal output portion;

a standard time output portion for outputting a standard time which is a basis for judging whether or not said luminance setting portion should change said luminance of said stimulus; and a time comparison portion for comparing said response time and said standard time with each other;

wherein said luminance setting portion darkens said luminance of a stimulus to be next presented at the position by a first predetermined volume if said time comparison portion judges said response time to be shorter than said standard time, and darkens said luminance of a stimulus to be next presented at the position by a second predetermined volume if said time comparison portion judges said response time to be longer than said standard time and shorter than a constant time, and lightens said luminance of said stimulus if said time comparison portion judges said response time to be longer than said constant time, wherein said displayed position change portion changes said displayed position of said stimulus if said time comparison portion judges said response time to be longer than said constant time.

4. The ophthalmic testing unit according to claim 3, wherein said first predetermined volume is more than said second predetermined volume.

5. The ophthalmic testing unit according to claim 3, wherein said stimulus presentation portion is comprised of a projection optical system for projecting said stimulus and a projection member on which said stimulus is projected by said projection optical system.

* * * * *

UNITED STATES PATENT AND TRADEMARK OFFICE
CERTIFICATE OF CORRECTION

PATENT NO.        : 7,393,104 B2                                      Page 1 of 1
APPLICATION NO.   : 11/238367
DATED             : July 1, 2008
INVENTOR(S)       : Takuya Hara It is certified that error appears in the above-identified patent and that said Letters Patent is hereby corrected as shown below:

On page 1, column 2, (Assistant Examiner), delete "Dawayne" and insert --DaWayne--, therefor In claim 1, line 36, delete "means:" and insert --means;--, therefor In claim 1, line 42, delete "other:" and insert --other;--, therefor In claim 3, line 57, delete "exarninee" and insert --examinee,--, therefor In claim 3, column 2, line 3, delete "iudges" and insert --judges--, therefor In claim 3, column 2, line 7, delete "iudges" and insert --judges--, therefor Signed and Sealed this Seventh Day of April, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,393,104 B2  
APPLICATION NO. : 11/238367  
DATED : July 1, 2008  
INVENTOR(S) : Takuya Hara Page 1 of 1

It is certified that error appears in the above-identified patent and that said Letters Patent is hereby corrected as shown below:

On page 1, column 2, (Assistant Examiner), delete "Dawayne" and insert --DaWayne--, therefor In claim 1, column 19, line 36, delete "means:" and insert --means;--, therefor In claim 1, column 19, line 42, delete "other:" and insert --other;--, therefor In claim 3, column 20, line 57, delete "exarninee" and insert --examinee,--, therefor In claim 3, column 22, line 3, delete "iudges" and insert --judges--, therefor In claim 3, column 22, line 7, delete "iudges" and insert --judges--, therefor This certificate supersedes the Certificate of Correction issued April 7, 2009.

Signed and Sealed this

Twenty-eighth Day of April, 2009

JOHN DOLL  
*Acting Director of the United States Patent and Trademark Office*